(12) United States Patent
Toda

(10) Patent No.: US 7,171,612 B2
(45) Date of Patent: Jan. 30, 2007

(54) MEDICAL IMAGE PROCESSING APPARATUS AND MEDICAL NETWORK SYSTEM

(75) Inventor: Haruyuki Toda, Tokyo (JP)

(73) Assignee: Konica Corporation, Tokyo (JP)

( * ) Notice: Subject to any disclaimer, the term of this patent is extended or adjusted under 35 U.S.C. 154(b) by 450 days.

(21) Appl. No.: 10/147,265

(22) Filed: May 15, 2002

(65) Prior Publication Data

US 2002/0175910 A1   Nov. 28, 2002

(30) Foreign Application Priority Data

May 23, 2001   (JP) .............................. 2001-153342

(51) Int. Cl.
   *G06N 3/00*   (2006.01)
(52) U.S. Cl. .................................................. 715/500
(58) Field of Classification Search ................ 715/513, 715/517, 500, 523, 530, 619, 501.1; 707/205; 345/619; 382/132, 235, 284; 710/54
See application file for complete search history.

(56) References Cited

U.S. PATENT DOCUMENTS

| | | | |
|---|---|---|---|
| 3,859,527 A | | 1/1975 | Luckey |
| 4,692,806 A * | | 9/1987 | Anderson et al. ....... 375/240.08 |
| 5,325,449 A * | | 6/1994 | Burt et al. ................... 382/240 |
| 5,671,429 A * | | 9/1997 | Tanaka ........................ 715/530 |
| 5,734,915 A * | | 3/1998 | Roewer ...................... 715/512 |
| 5,745,121 A * | | 4/1998 | Politis ......................... 345/619 |
| 5,857,199 A * | | 1/1999 | Tamano et al. ........... 707/104.1 |
| 5,860,066 A * | | 1/1999 | Rouse ............................. 705/1 |
| 5,995,724 A * | | 11/1999 | Mikkelsen et al. ......... 358/1.16 |
| 6,396,500 B1 * | | 5/2002 | Qureshi et al. .............. 345/473 |
| 6,538,765 B1 * | | 3/2003 | Ikedo ......................... 358/1.16 |
| 6,590,674 B1 * | | 7/2003 | Orton ......................... 358/1.18 |
| 6,593,935 B2 * | | 7/2003 | Imaizumi et al. ........... 345/619 |
| 6,633,890 B1 * | | 10/2003 | Laverty et al. ............. 707/203 |
| 6,671,394 B1 * | | 12/2003 | Sako ........................... 382/132 |
| 6,683,619 B1 * | | 1/2004 | Samra ......................... 345/619 |
| 6,772,396 B1 * | | 8/2004 | Cronin et al. ............... 715/523 |

(Continued)

FOREIGN PATENT DOCUMENTS

JP   55-012144   1/1980

OTHER PUBLICATIONS

"Segmentation Fault," <http://web.archive.org/web/20000829095934/http://cs-www.bu.edu/unix/segmentation_fault.html>, Aug. 29, 2000, p. 1.*
Stytz et al. "Three-Dimensional Medical Imaging: Algorithms and Computer Systems," Dec. 1991, ACM Computing Surveys, vol. 23, No. 4, pp. 421-499.*
Conklin, "queue.mac," 1973, Digital Equipment Corp., pp. 1-88.*

(Continued)

*Primary Examiner*—Cesar Paula
*Assistant Examiner*—Kyle Stork
(74) *Attorney, Agent, or Firm*—Frishauf, Holtz, Goodman & Chick, P.C.

(57) ABSTRACT

A medical image processing apparatus for receiving an image file including medical image information, and for processing the medical image information so as to output a processed image file. The medical image processing apparatus includes: an output queue controller for controlling an output queue to define an order for outputting plural image files; an auxiliary controller for controlling a supplementary queue to supplement the output queue; and an output apparatus for outputting at least the plural image files. A medical network system is also configured for connectting, through a network, the medical image processing apparatus and an input apparatus to which the processed image file is inputted.

7 Claims, 5 Drawing Sheets

U.S. PATENT DOCUMENTS

2001/0019430 A1* 9/2001 Shiota et al. ............... 358/487
2002/0002568 A1* 1/2002 Judson ....................... 707/513
2002/0016972 A1* 2/2002 Ogawa et al. .............. 725/133
2002/0019832 A1* 2/2002 Tanaka et al. .............. 707/500
2002/0099732 A1* 7/2002 Miller et al. ............. 707/501.1
2003/0140309 A1* 7/2003 Saito et al. ................. 715/500

OTHER PUBLICATIONS

"Class GenericFilterAgentImpl," <http://hive.sourceforge.net/hive-javadoc/devel/net/hivecell/hive/agent/image/GenericFilterAgentImpl.html>, 2000, pp. 1-5.*

Tanenbaum, Andrew S., "Modern Operating Systems: Second Edition," 2001, Prentice Hall, pp. 196-202.*

* cited by examiner

MEDICAL IMAGE PROCESSING APPARATUS AND MEDICAL NETWORK SYSTEM

BACKGROUND OF THE INVENTION

The present invention relates to a medical image processing apparatus and to a medical network system including the medical image processing apparatus.

Radiation images are widely used in a diagnosis for sickness, and for the purpose of obtaining the radiation images, there is known a method wherein radiations emitted from a radiation exposure section and transmitted through an object are absorbed in a plate-shaped stimulable phosphor, then, the stimulable phosphor is scanned by a laser beam, for example, to be excited, and radiation energy (radiation image information) accumulated in the stimulable phosphor through its absorption are emitted as fluorescence, and this fluorescence is converted photoelectrically so that radiation images are read by obtaining radiation image signals (U.S. Pat. No. 3,859,527 and TOKKAISHO No. 55-12144). Patent No. Stimulable emitted light generated from the stimulable phosphor plate is converged by the scanning of the laser beam, then it is converted photoelectrically by a photo-multiplier and this electric signal is amplified, thus, radiation images are read based on the digital signal obtained by the conversion from the analog signal.

When an image file is sent from a medical image generating apparatus that reads and generates a medical image as stated above, and when a plurality of image files are sent to an image outputting apparatus for forming images on a film to output them, after the image file is received by an image processing apparatus and is processed therein, the image files are outputted in succession beginning with the forefront image file on the administration table called a queue. In this case, in the case of a multi-image format for forming plural image files on a film by arranging them with an image outputting apparatus, multi-image format images are registered on the queue after they are made, and the multi-image format images are outputted only when the images are continuous. Further, when making an image file for the purpose of outputting that is image-processed by an image outputting apparatus to be compatible with an output format, the image file for the purpose of outputting is made to be compatible with an output format for each target of output for the image outputting apparatus.

In the case of the multi-image format, however, it is necessary to make a multi-image format image file separately from a plurality of original images because multi-image format images are registered after they are made in advance, resulting in necessity of additional capacity on a memory for a separate file, and changes of the original images are not reflected after the multi-image format images are made.

When continuous images are outputted on a multi-image format basis, it is necessary for a user to make the continuous images to be registered with a queue, taking the order of the images into consideration, which results in complicated operations for the registration.

Further, in the case of outputting an image to a plurality of image outputting apparatuses, making an image file to be compatible with an outputting mode for each target for output is wasteful consumption of memory capacity and is time-consuming, which is not efficient occasionally.

SUMMARY OF THE INVENTION

An object of the invention is to provide a medical image processing apparatus wherein consumption of memory capacity is not increased when outputting multi-image format images, changes of original images are reflected on the multi-image format images until the moment just before outputting, ease of use is achieved when output of multi-image format images is designated, and wasteful image files are not made and capacity of the memory and time can be utilized efficiently when an image is outputted to a plurality of image outputting apparatuses and to provide a medical network system.

For attaining the object mentioned above, the first medical image processing apparatus of the invention is a medical image processing apparatus that receives an image file including medical image information, and processes the image information to output it, and it is characterized in that a means to control an output queue for controlling the order for outputting image files, a means to control a multi-image format queue for controlling the order for outputting image files formatted in a multi-image format composed of plural images, a means wherein, when an image file designated on the multi-image format comes to the forefront of the output queue, that image file is not outputted by the output queue control means, but is registered momentarily with the multi-image format queue, and a means that generates multi-image format images with the multi-image format queue control means to output them when all of plural image files constituting the multi-image format are registered on the multi-image format queue are provided.

In this first medical image processing apparatus, multi-image format images are generated and outputted after all image files constituting the multi-image format are registered on the multi-image format queue. Therefore, changes of each image file representing the original image are reflected on multi-image format images until the moment just before the outputting, and it is not necessary to store multi-image format image files in the memory separately from the plural original images, thereby, consumption of memory capacity is not increased. Further, when designating output of multi-image format images, queue registration for considering the order is not needed, and therefore, ease of operation is achieved and erroneous operations of wrong order can be prevented.

The second medical image processing apparatus of the invention is a medical image processing apparatus that receives an image file including medical image information, and processes the image information to output it, and it is characterized in that a means to control a formatting queue for controlling the order for generating image file for output so that a prescribed output format may be provided from an image file, a means to control output queue for controlling the order for outputting image files for output, a means to compare an output format for each target for output in the case of plural designated output targets when the image file comes to the forefront of the formatting queue for the output in quantity corresponding to different output formats, and to make image files for output in quantity corresponding to the different output formats, a means to register one or more image files for output thus made on the output queue by the use of the output queue control means, and a means to output the image file for output on the forefront of the output queue, are provided.

In this second medical image processing apparatus, image files in quantity corresponding to the modes of different output targets are made. Therefore, in the case of the same output format, image files for output are not made in spite of plural output targets. Accordingly, when an image is outputted to plural output targets in the same output format, wasteful image files do not need to be made, and memory capacity and time can be utilized efficiently.

In the second medical image processing apparatus, it is preferable that, when plural output targets are present for the image file for output, all outputs are judged whether they are completed or not, and the image files for output are not eliminated until all outputs are completed based on the results of the judgment.

It is preferable that a storage means for registering the image files for output is provided on the output queue, and the image files for output are not are not made when an residual capacity for storage of the storage means becomes equal to or lower than the residual capacity for storage established in advance. Due to this, a prescribed storage capacity can be ensured constantly, because an residual capacity of the storage means is always equal to or more than a prescribed amount. It is also possible to arrange so that the image file for output may not be made when the sum total of file sizes of the image files for output comes to the size established in advance or more.

The first medical network system of the invention is a medical network system structured to be connected, through the network, to a medical image processing apparatus that receives an image file including medical image information and processes the image information and to an input apparatus into which an image file outputted from the medical image processing apparatus is inputted, and it is characterized in that a means to control an output queue for controlling the order for outputting image files, a means to control a multi-image format queue for controlling the order for outputting image files formatted in a multi-image format composed of plural images, a means wherein, when an image file designated on the multi-image format comes to the forefront of the output queue, that image file is not outputted by the output queue control means, but is registered momentarily with the multi-image format queue, and a means that generates multi-image format images with the multi-image format queue control means to output them when all of plural image files constituting the multi-image format are registered on the multi-image format queue, are provided.

In this first medical network system, multi-image format images are generated and outputted after all image files constituting the multi-image format are registered on the multi-image format queue. Therefore, changes of each image file representing the original image are reflected on multi-image format images until the moment just before the outputting, and it is not necessary to store multi-image format image files in the memory separately from the plural original images, thereby, consumption of memory capacity is not increased. Further, when designating output of multi-image format images, queue registration for considering the order is not needed, and therefore, ease of operation is achieved and erroneous operations of wrong order can be prevented.

The second medical network system of the invention is a medical network system structured to be connected, through the network, to a medical image processing apparatus that receives an image file including medical image information and processes the image information and to an input apparatus into which an image file outputted from the medical image processing apparatus is inputted, and the medical image processing apparatus is characterized in that a means to control a formatting queue for controlling the order for generating image files for output so that a prescribed output format may be provided from the image file, a means to control output queue for controlling the order for outputting the image files for output, a means to compare an output format for each output target and makes image files for output in quantity corresponding to the different output formats in the case of plural designated output targets when the image file comes to the forefront of the formatting queue, a means to register one or more image files for output thus made on the output queue with the output queue control means, and a means to output the image file for output positioned at the forefront of the output queue, are provided.

In this second medical network system, image files for output in quantity corresponding to the modes of different input apparatuses are made. Therefore, in the case of the same output format, image files for output are not made in spite of plural input apparatuses. Accordingly, when an image is outputted to plural input apparatuses in the same output format, wasteful image files do not need to be made, and memory capacity and time can be utilized efficiently.

DETAILED DESCRIPTION OF THE INVENTION

Figure 1:
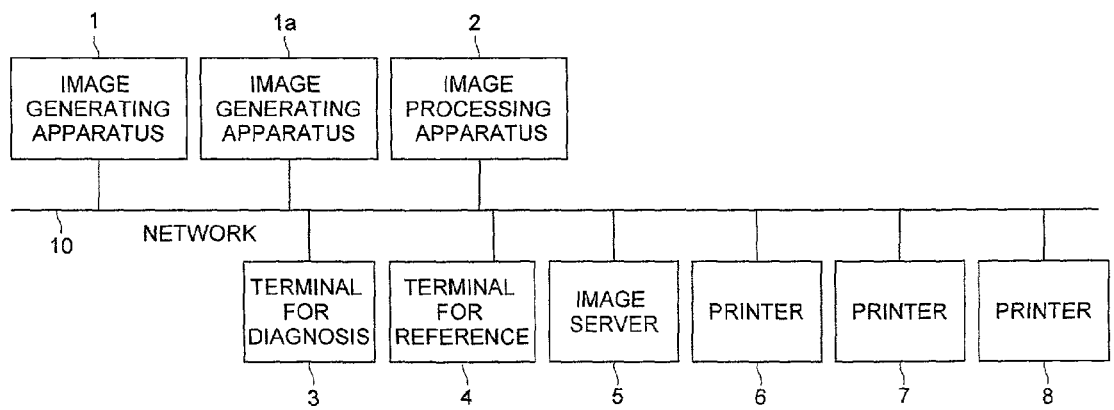
FIG. 1 is a diagram showing the structure of a medical network system of the present embodiment of the invention.

A medical network system of the present embodiment of the invention will be explained as follows, referring to the drawings. FIG. 1 is a diagram showing the structure of the medical network system of the present embodiment of the invention.

The medical network system shown in FIG. 1 is provided with medical image generating apparatus 1 wherein a medical image is generated by a radiographing modality of CR (computed radiography) that scans a stimulable phosphor panel in which radiographic image information of a subject (patient) is recorded to make it to emit light and transfers the light photoelectrically to obtain image information, medical image processing apparatus 2 that inputs an image file from the medical image generating apparatus 1 and the medical image generating apparatus 1a and outputs image information after conducting image processing, and with terminal for diagnosis 3 that is composed of a personal computer and a work station, and is used by a radiologist to diagnose by referring to images.

The medical network system shown in FIG. 1 is further provided with terminal for reference 4 that is composed of a personal computer and a workstation displaying images, and is inferior in quality such as resolution compared with the terminal for diagnosis 3 because no diagnosis is made although images are referred to, image server 5 that is composed of a personal computer and a workstation, and can store an image file in image data base and can detect images from the terminal for diagnosis 3 and from the terminal for reference 4 to read them, and with plural printers 6, 7 and 8 each receiving image data from the medical image generating apparatus 1 or the medical image processing apparatus 2 and outputs a visible image on a recording medium such as a film or a sheet of paper. Each of the items 1–8 stated above is connected on an on-line connection basis through the network 10, so that information may be transmitted and received mutually.

Figure 2:
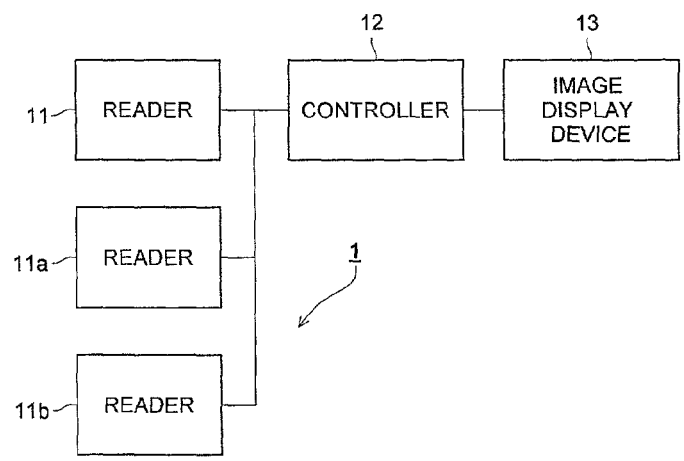
FIG. 2 is a block diagram showing the structure of medical image generating apparatus 1 shown in FIG. 1.
Figure 4:
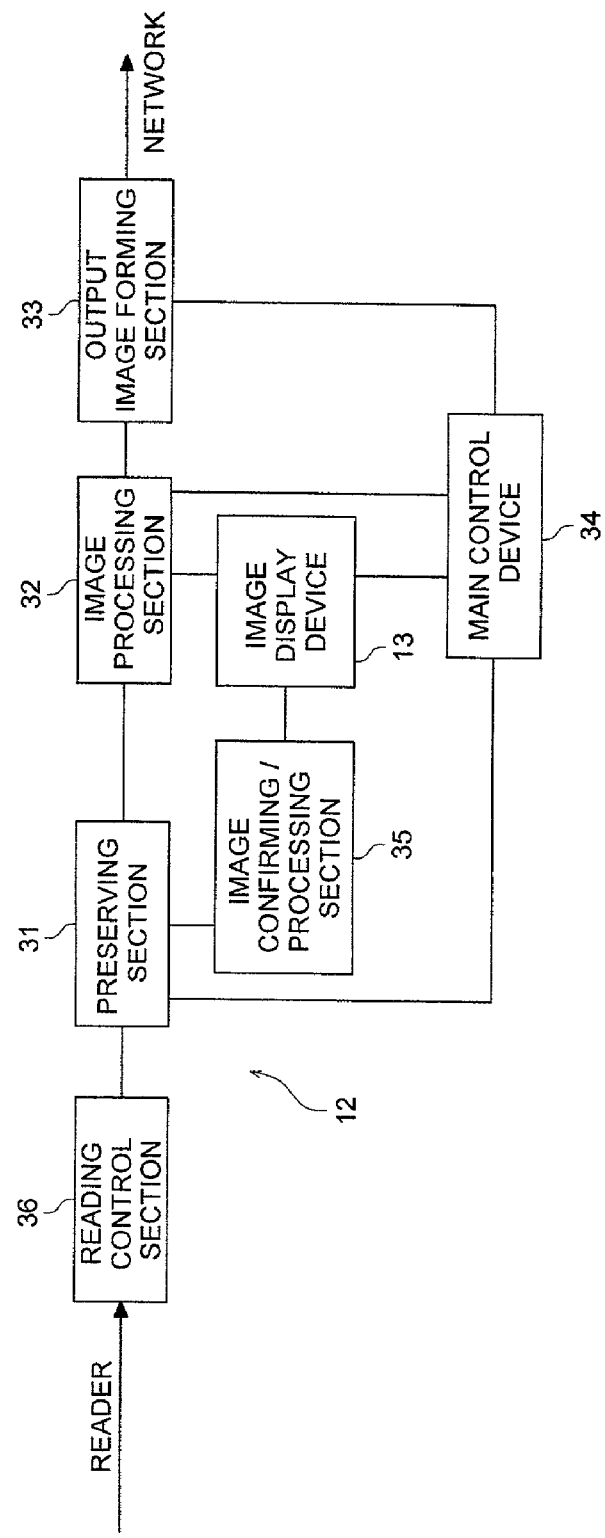
FIG. 4 is a block diagram of a controller of medical image generating apparatus 1 shown in FIG. 2.

Next, medical image generating apparatus 1 shown in FIG. 1 will be explained as follows, referring to FIGS. 2 and 4. FIG. 2 is a block diagram showing the structure of medical image generating apparatus 1, and FIG. 4 is a block diagram showing the structure of a controller shown in FIG. 2. Incidentally, image generating apparatus 1a is also of the same structure as in the foregoing.

As shown in FIG. 2, the medical image generating apparatus 1 is provided with radiographic image inputting apparatus (reader) 11 that converts information read from a stimulable phosphor panel on which radiographic image information of an object (patient) is accumulated and recorded to obtain, controller 12 that controls operations of the whole radiographing system for radiographic images, and image display device 13 that is composed of a CRT display or of a liquid crystal panel and displays digital image data obtained by the reader 11. Incidentally, the medical image generating apparatus 1 includes information inputting devices such as an input key board and a mouse.

The medical image generating apparatus 1 is provided with reader 11a which obtains by converting, into digital image data, the information obtained through reading from a stimulable phosphor panel in a radiographing apparatus of a standing type that radiographs a standing patient, and reader 11b which obtains by converting, into digital image data, the information obtained through reading from a stimulable phosphor panel in a radiographing apparatus of a lying type that radiographs a lying patient.

The controller 12 constitutes a man-machine interface which is operated by a user (radiologist), and controls the whole of the medical image generating apparatus 1. As shown in FIG. 4, the controller 12 includes reading control section 36 that receives image data from readers 11, 11a and 11b and conducts correction processing on a real time basis, preserving section 31 that is composed of a hard disc or RAM and stores and preserves various types of information such as image files from the reading control section 36, image processing section 32 that conducts image processing for image information in the image files, output image forming section 33 that forms output images to be outputted to the outside, image confirming/processing section 35 that conducts image processing for image confirmation and makes display device 13 to display reduction images, and main control apparatus 34 that controls operations of the whole apparatus including various sections 31–33 and 35 and the display device.

The controller 12 conducts the following operations 1)–7) to be concrete.
1) A user operates for an appointment of radiographing.
2) A user operates for radiographing.
3) To receive image data obtained through reading by readers 11 and 11a.
4) To preserve image data in preserving section 31 temporarily.
5) To conduct image processing at image processing section 32.
6) To form output images at output image forming section 33.
7) To transmit to an outer apparatus such as image server 5 through the network 10.

Figure 3:
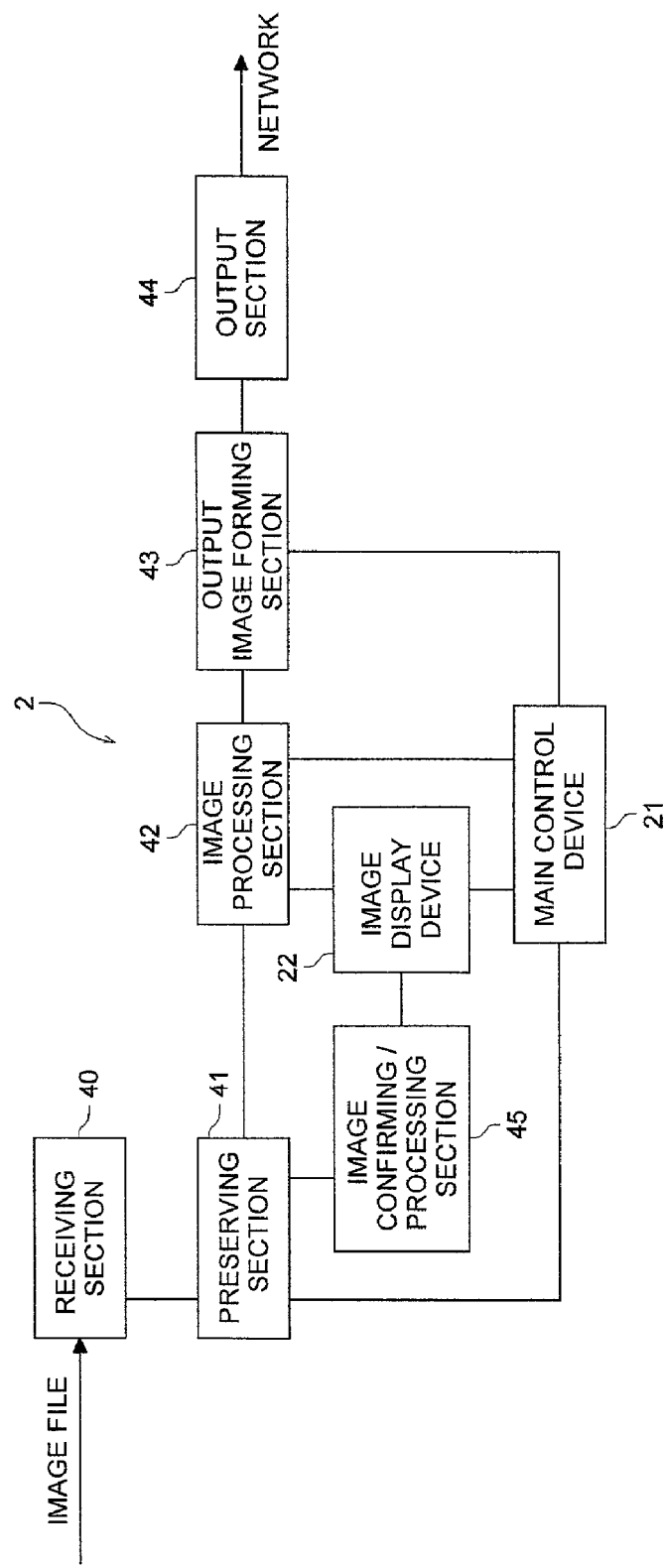
FIG. 3 is a block diagram showing the structure of medical image processing apparatus 2 shown in FIG. 1.

Next, the following items A–H relating to medical image generating apparatus 2 in FIG. 1 will be explained in detail successfully.
A. Apparatus structure
B. Information
C. File
D. Input and display of main information
E. Image confirming procedures
F. Output
G. Output image formation
H. Utility function A. Apparatus Structure FIG. 3 is a block diagram showing the structure of medical image processing apparatus 2.
a. The medical image processing apparatus 2 shown in FIG. 3 is provided with main control apparatus 21 that controls operations of the whole radiographing system for radiographic images, and with image display device 22 that is composed of a CRT display or of a liquid crystal panel and displays digital image data obtained by medical image generating apparatus 1, and it can be composed of a personal computer and includes information inputting device such as an input key board and a mouse.

As shown in FIG. 3, the image processing apparatus 2 further includes receiving section 40 that receives image files from image forming apparatuses 1 and 1a, preserving section 41 that is composed of a hard disc or RAM and stores various pieces of information such as an order of received image files and output queue, image processing section 42 that conducts image processing for image information in the image files, output image forming section 43 that forms output images to be outputted to the outer apparatuses, output section 44 that outputs output images in succession to terminal for diagnosis 3 in FIG. 1, terminal for reference 4 and to outer apparatuses such as a host computer of image server 5 and printers 6–8, through network 10, while administrating them by a queue, and image confirming/processing section 45 that makes image display device 22 to display reduced images for confirmation of received images. Main control apparatus 21 controls each of sections 40–44 and the display device 22.

b. The functions of the medical image processing apparatus 2 are as follows, and each function is controlled by the main control apparatus 21.
1) To receive image files from medical image generating apparatus 1 or the like at receiving section 40.
2) To preserve image files in preserving section 41 temporarily.
3) To confirm image quality by the use of reduced images prepared by image confirming/processing section 45.
4) To conduct image processing on the image processing section 42.
5) To form output images at output image forming section 43.
6) To transmit output images to outer apparatuses such as image server 5 and printers 6–8 through the network 10.

B. Information

Information handled by the medical image processing apparatus 2 can be classified into the following five types of information.

a. Condition Information

The condition information is one necessary for receiving image files, and for outputting to an outer apparatus such as image server 5 as a processed image file, and it includes the following.

(a) Image Processing Information

This is information relating to gradation processing and frequency processing in image processing section 42.

(b) Outputting Apparatus Information

This is information relating to outer outputting apparatuses such as image server 5 which reproduces and outputs image data, and it designates an area to be outputted, magnification and rate of reduction, output format (multi-format, split radiographing format), overlay and existence of gradation processing and frequency processing for each outputting apparatus such as image server 5.

(c) Overlay Information

This is information about existence and position of overlay such as AP/PA, R/L and comment.

(d) Information About Specific Designation

Information of protection: Image files are preserved until protection is removed, even after the image transmission.

Information of pending: Transmission is reserved. This is designated when transmission is needed after the image is reviewed.

Information of priority (emergency): This is designated when preferential output such as emergency radiographing is required. This is registered to be at the forefront of a cue.

b. Patient Information

This is information concerning patients.

(a) Patient ID Information

An ID number, a full name, the distinction of sex and the date of birth of a patient.

(b) Order Information

This is information with which a doctor requests radiographing, which includes information relating to patient conditions and instructions for the date and method for the inspection requested.

c. Information of Radiographing Implementation

This is information concerning the results of receiving an image processing.

(a) The results of receiving and the date of radiographing are included.

(b) Results of Image Processing

This is a result of calculation of image processing parameter, and image data are processed based on this result when outputting.

(c) System Information

This includes a part of system information such as a system structure at the point of time when radiographing is conducted.

d. System Information (a) Information for controlling the system in FIG. 1

(b) Structures of system in FIG. 1 (outer apparatus such as image server 5 connected, and its name)

(c) Parameter and table to control equipment constituting the system in FIG. 1

(d) Setting information concerning medical image generating apparatus 1 representing an inputting apparatus (e) Setting information concerning an outputting apparatus such as information of imager 6 and HOST information e. Image Data (a) Image data received from medical image generating apparatus 1

(b) Reduction image data for display prepared from image data for image confirmation.

(c) Reduction image data for image processing for image processing of reduction image for display at image confirming/processing section 45.

(d) Output image data which have been subjected to gradation processing and frequency processing.

C. File

A file handled by medical image processing apparatus 2 is preserved in preserving section 41, and it is classified into the following seven files.

a. Condition File

A condition key is a key for setting in advance image processing conditions for image files and outing conditions. It has a condition file that corresponds to each condition key. The condition file is composed of the radiographing information above mentioned. It is classified in terms of radiographing regions (lung, abdomen, head and others), radiographing posture (standing posture, lying posture and others), radiographing direction (front, side and others), characteristics of a patient (the distinction of sex, age, physical structure and others), the name of a disease and a radiologist, and a name and radiographing information corresponding to each of them are established in advance. Main control apparatus 21 establishes a condition file group for each of classified plural classifications, then, sets plural condition files for each condition file group thus established, and preserves in preserving section 41. The optimum condition is selected in the course of receiving images.

b. Image Header File

After receiving, an image header file is prepared. The header file is composed of a reservation file of the radiographing (namely, radiographing information, patient information) and information of conducting radiographing. When a user refers to radiographing information, patient information and information of conducting radiographing for changing, the user refers to an image header file.

c. Reduction Image File

This represents image data which are obtained by reducing image data at a certain reduction ratio.

(a) Reduction Image Data for Display

This reduction image for display is used by data displayed on image display device 22 in FIG. 3.

(b) Reduction Image Data for Image Processing

This represents reduction image data for calculating a parameter that is for conducting image processing. The reduction rate is determined so that a length of one pixel after reduction may be the same as a length designated in advance. Due to this, it is possible to correct the difference in a size of a pixel to be read with the image after being reduced. Calculation of a parameter for image processing is conducted by the reduction image for image processing, and image data are not used.

d. Image File (a) An image file is composed of image-accompanying information (image header) and image data.

(b) An image header is composed of condition information, patient information and implementation information. When a user makes a change by referring to condition information, patient information and implementation information, the user refers to the image header.

e. Output Image File

This is a file of output image data which have been subjected to the designated processing among frequency processing, gradation processing, overlay, rotation and enlargement and reduction.

f. System File

This is one wherein the system information mentioned above is made to be of a type of a file.

D. Input and Display of Primary Information a. Received Image Information Display Received images are displayed on a thumbnail mode.

b. Output Information Display

1) An outputting size, a direction, a trimming position, an outputting position and a method of enlargement and reduction are designated, and registered in a condition file in advance.
2) When a condition key is selected, the output area and output image area are determined under the condition designated in advance, and are displayed on the screen of the image display device 22. A size of the output area display area on the screen of the image display device 22 is made to be the maximum output area in outputting. An output area and an output image area are displayed graphically on the output area display area. Due to this, the appropriate output area and the output image area can be selected and confirmed.

c. Overlay Information

1) It is designated whether or not "AP", "PA", "R", "L", comment and a division are overlaid, or where they are overlaid, and they are registered in a condition file in advance.
2) Output images are displayed on an output area display area on the screen of the image display device 22, and overlay information is displayed graphically there.
3) It is possible to select an appropriate overlay and to designate a position.
4) It is possible to confirm that a portion screened by the overlay to be invisible is not present. When the overlay causes troubles on diagnoses, it can be moved.

d. Inputting and Outputting of On-line Information from RIS

1) Orders from a doctor are inputted. The orders thus inputted are converted into the format of this system to be preserved in the reservation file. The radiographing region and radiographing method are converted into corresponding radiographing conditions.
2) An image header file is converted into the format on the RIS side, and outputted.

e. Image List

An image file can be displayed as a list.

E. Image Confirming Procedures a. Operations of System in Image Confirmation (1) An image file is received from medical image generating apparatus 1, and is stored in preserving section 41.
(2) The image file stored in a storage medium of the preserving section 41 is reduced at the reduction rate designated by image confirming/processing section 45 in advance.
(3) Reduction images are displayed successively on the screen of image display device 22.
(4) After receiving and completion of display, digital image information is subjected to image processing in the method designated in advance by a radiographing condition key, and is displayed again on image display device 22. Reduction images are used to determine a parameter for image processing.
(5) Images which are displayed successively on the image display device 22 and are subjected to gradation processing after being displayed are displayed again.
(6) When an operator observes received images displayed on the image display device 22 and judges that they are normal images, a key for confirming the completion of receiving is inputted from a character information inputting apparatus, thus, image confirmation is completed.
(7) When patient information, image processing methods and output methods need to be changed, it is possible to input new information from a character information inputting apparatus.
(8) When an image confirming key is pressed, image confirmation for that image is completed, and the following image is displayed automatically.
(9) When an image has a problem, it is possible to change image processing. By reserving it, it is possible to change image processing in detail later.
(10) When an image confirming key is inputted, image confirmation is completed, and the following processing is conducted.
  1) The image file is preserved in preserving section 41 as a confirmed image file.
  2) Images whose image confirmation has been finished are registered in a cue for outputting to an outer apparatus.
  3) Then, the received image file is displayed so that images may be confirmed.
(11) When a reservation key is inputted, image confirmation is completed.

F. Output

1) Output is conducted on a non-synchronization basis with image confirmation.
2) Though a cue is made and controlled for each outer apparatus, plural printers 6–8, for example, are sometimes controlled by one as will be stated later.
3) The whereabouts of the image in terms of registration in a cue of an outer apparatus is preserved in preserving section 41 as a cue registration table, and it is updated and controlled for each registration and cancellation.
4) An image registered in the cue is outputted to an outer apparatus in the order of registration, and the image whose outputting is finished is deleted from the cue.
5) When carrying out outputting, an image file stored in preserving section 41 is specified from numbers registered in the cue.
6) An output image is formed under the condition preserved in the image file. The image header is converted into the format determined for each outputting apparatus, and is transmitted together with image data.

G Forming Output Image a. An output image is formed by output image forming section 43 mainly through the following processing.
1) Image data are read from preserving section 41 to a memory for images.
2) Frequency processing is conducted.
3) Equalization processing is conducted.
4) Gradation processing is conducted.
5) Rotation of an image is carried out.
6) Mirror reversing is conducted.
7) Enlargement and reduction are carried out.
8) Overlay is carried out.

b. With respect to each of 2)–8), whether it is executed or not can be designated by condition information for each outputting apparatus.

c. It is possible to designate that image data subjected to designated processing of each of 2)–8) are preserved as processed image data file. Re-processing of common processing section of output image for each output apparatus is removed.

d. For example, when an enlargement rate and a reduction rate of an output image for each output apparatus are different from others, if images which have been subjected to processing up to 6) are preserved, it is possible to shorten a period of time for 2)–6) by reading images which have been subjected to processing up to 6) and by processing and transferring only 7) and 8), when transmitting to another apparatus.

e. Processing 5) and 6) are conducted simultaneously with either one of 2), 3) and 4). Access of memory is reduced, and processing time can be shortened.

H. Utility Function a. As a utility for a user, some functions are provided thereto. Utility function is restricted by a password for each of general user, a manager and a maker. In particular, for a change of information relating to images, a password of a manager is required for security.

b. Image File Operation

1) An image file list is displayed, and information concerning images preserved is displayed on image display device 22 in the order of receiving.
2) When a desired image is selected from the list, patient information, condition information and images are displayed in the same form as in the screen in the case of image confirmation.
3) Patient information, image processing methods and outputting methods can be changed.
4) With regard to the image designated to be "reservation" in the case of radiographing, the "reservation" can be canceled by reconfirming here.
5) The order of outputting can be changed, including whether outputting to each outer apparatus is conducted or not.

c. Radiographing Record, Emission Record

1) Radiographing information and patient information are processed statistically, and are provided to a user as a radiographing record and an emission record.
2) The number of shots per each radiographing region for a designated period and a list of radiographing conditions for shots per day can be outputted.

d. Customizing

A screen and operating procedures can be customized for each user.

Next, an output of an image file from a medical image processing apparatus in the medical network system in FIGS. 1 and 3 will further be explained as follows, referring to FIG. 5.

Figure 5:
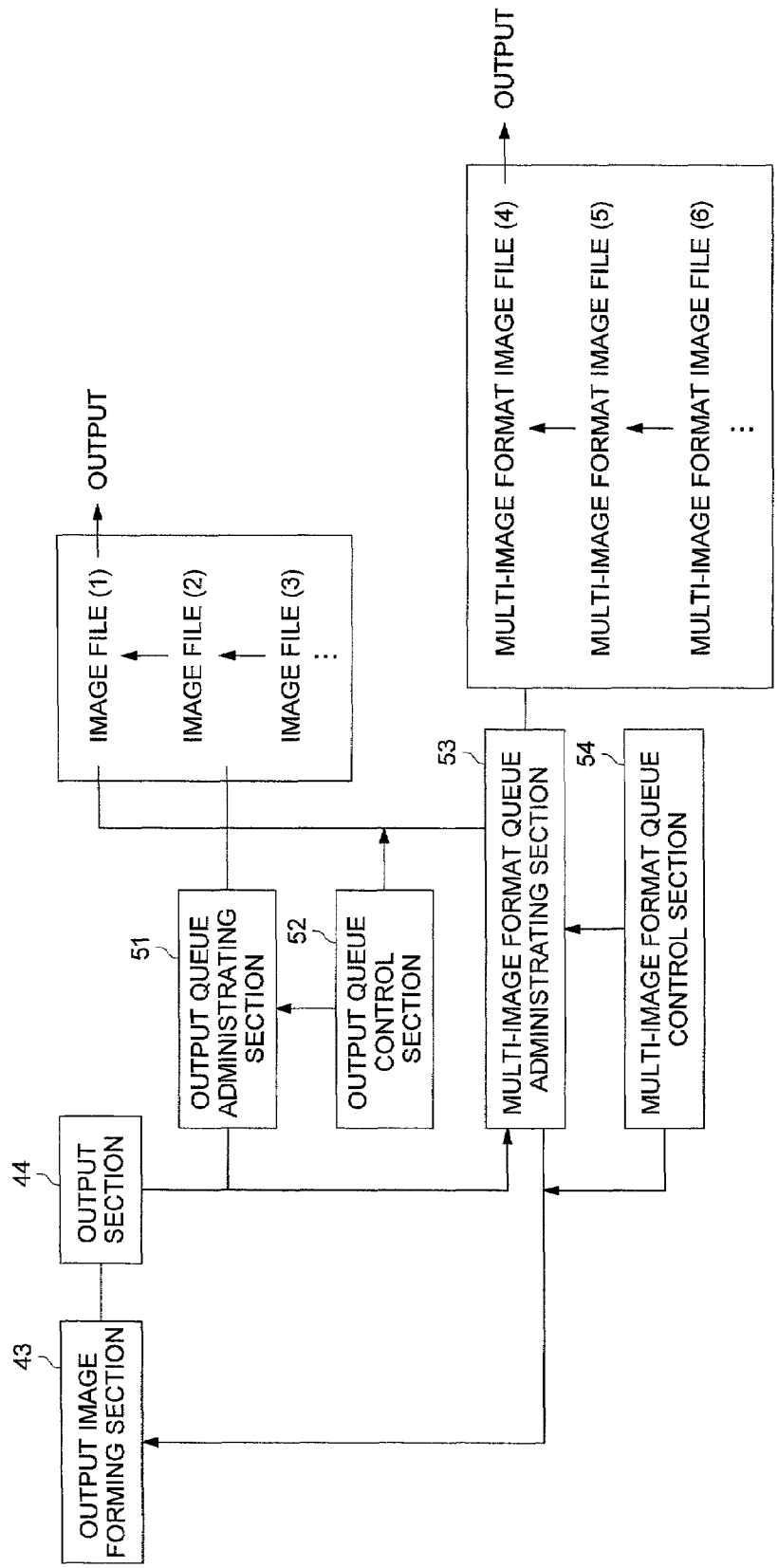
FIG. 5 is a block diagram for illustrating how to control when outputting a multi-image format image file at output image forming section 43 and output section 44 in FIG. 3.

FIG. 5 is a block diagram for illustrating the control in the case of outputting a multi-image format image file in output image forming section 43 and outputting section 44 in FIG. 3. Incidentally, the multi-image format is a format, for example, to print a plurality of images on a single sheet of film, in the following mode.

1×2 (2 images in lateral 1 row and longitudinal 2 line), 2×1 (2 images in lateral 2 row and longitudinal 1 line), 2×2 (4 images in lateral 2 rows and longitudinal 2 lines), 2×3 (6 images in lateral 2 rows and longitudinal 3 lines) . . . 4×5 (20 images in lateral 4 rows and longitudinal 5 lines)

As shown in FIG. 5, outputting section 44 of the medical image processing apparatus is provided with output queue control section 51 that controls the order for outputting image files so that image files 1), 2), 3), subjected to prescribed image processing in the order of receipt by output image forming section 43 in succession, output queue control section 52 that controls the output queue control section 51, multi-image format queue administrating section 53 that controls the order of outputting multi-image-format-designated image files so that multi-image format-designated image files may be outputted successively, and with multi-image format queue control section 54 that controls the multi-image format queue administrating section 53.

When a multi-image-format-designated image file comes to the forefront at the output queue control section 51 in FIG. 5, the multi-image-format-designated image file is outputted, through the control of output queue control section 52, to multi-image format queue administrating section 53 on a dummy basis without being outputted to an outer apparatus, and its outputting order is registered on the multi-image format queue administrating section 53. After the orders for all output for plural multi-image-format-designated image files have been registered on the multi-image format queue administrating section 53, multi-image format image files are generated by output image forming section 43 through the control of multi-image format queue control section 54, and multi-image format image files 4) are outputted from the multi-image format queue administrating section 53. In this way, multi-image format image files 5), 6), . . . are outputted in succession.

In FIG. 5, when image files 1) and 2) are designated to multi-image format, for example, and constitute multi-image format image file 4), the outputting order of the image files 1) and 2) is registered temporarily in multi-image format queue administrating section 53, and then, the multi-image format image file 4) is generated. Therefore, even if each of image files 1) and 2) representing original images is changed immediately before outputting, the change is reflected on a multi-image format image, and multi-image format image file 4) does not need to be stored in preserving section 41 (FIG. 3) each time, which does not increase an amount of capacity for consumption storage for memory in the preserving section 41. Further, when designating output of a multi-image format image file, queue registration in which the order is considered is not necessary, which ensures ease of operation and prevents erroneous operation of a wrong order.

Figure 6:
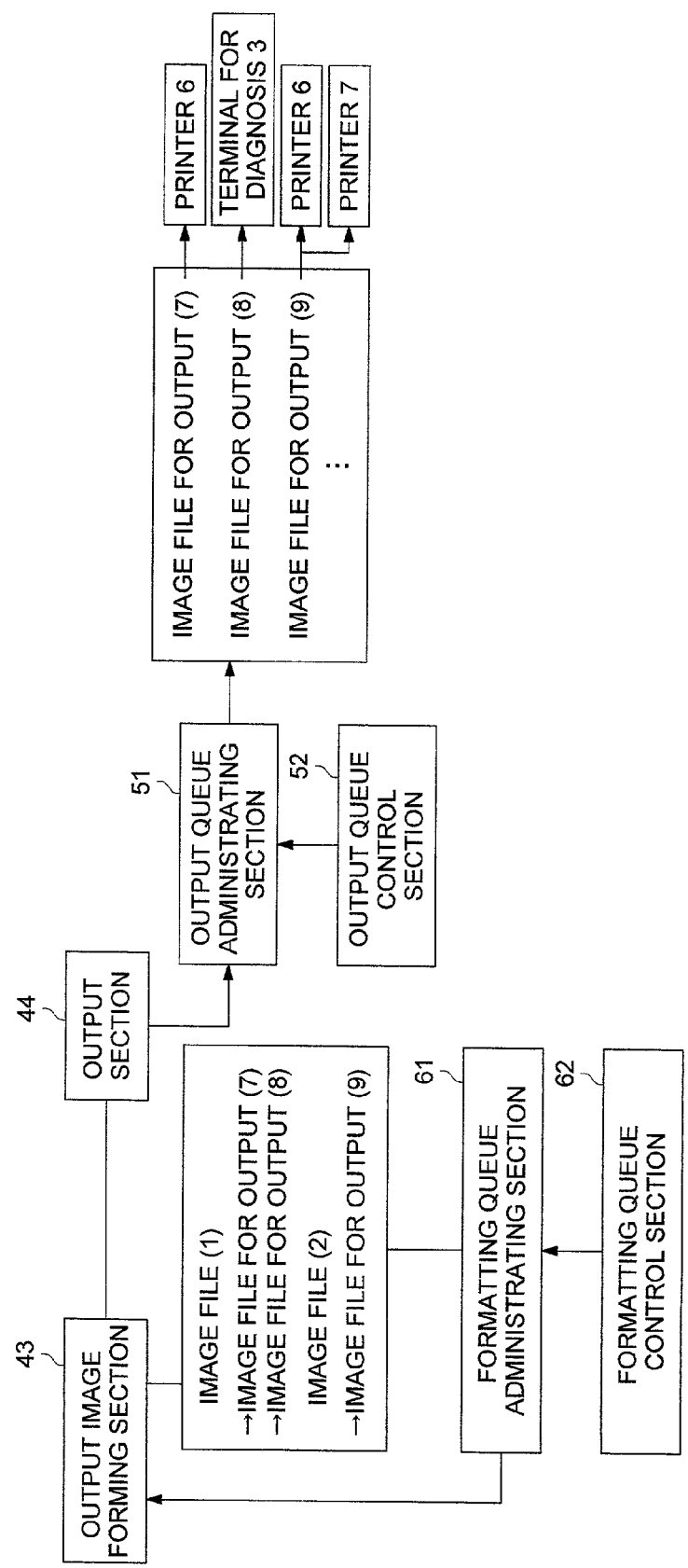
FIG. 6 is a block diagram for illustrating how to control when outputting an image file to plural output targets such as printers at output image forming section 43 and output section 44 in FIG. 3.

Next, another embodiment about image file outputting from a medical image processing apparatus will be explained referring to FIG. 6. FIG. 6 is a block diagram for illustrating the control in the case of outputting an image file to output targets such as a plurality of printers, in the output image forming section 43 and outputting section 44 in FIG. 3.

As shown in FIG. 6, the outputting section 44 of the medical image processing apparatus is provided with output queue administrating section 51 that administrates the outputting order for image files identical to those in FIG. 5 and with output queue controlling section 52 that controls the output queue administrating section 51, and it is further provided with formatting queue administrating section 61 that administrates the order for generating, from the image file, the image files for output so that outputting mode (outputting format) matched to a target for outputting such as a printer and with formatting queue administrating section 62 that administrates the formatting queue administrating section 61. In this case, the image file for output is a file of the image which has been subjected to image processing such as enlargement, reduction, trimming, gradation processing, frequency processing and overlay, in image output forming section 43 so that the processed image may match the final output format (output form).

For example, as shown in FIG. 6, image file 1) is outputted to printer 6 and to terminal for diagnosis 3, however, in the case of output formats which are different each other, when the image file 1) comes to the forefront of the queue at formatting queue administrating section 61, each output format is compared by formatting queue controlling section 62, image files for output 7) and 8) are prepared at output image forming apparatus 43, corresponding to different output format, and they are registered by output queue control section 52 on output queue administrating section 51. Then, when the image file 2) comes to the forefront of the queue at formatting queue administrating section 61, image files for output 9) only is prepared by formatting queue controlling section 62 at output image forming apparatus 43 if plural targets for output are printers 6 and 7 and if each output format is the same, and they are registered by output queue control section 52 on output queue administrating section 51.

When the image file for output 7) of image file 1) comes to the forefront of the output queue at output queue administrating section 51, it outputs to printer 6, and then, image file for output 8) of the same image outputs to terminal for diagnosis 3. Then, image file for output 9) of image file 2) comes to the forefront of the queue at output queue administrating section 51, therefore, it outputs to printer 6, and the same image file for output 9) outputs to printer 7.

In the aforesaid way, when a plurality of targets for output are present, image files for output in quantity corresponding to the number of different output forms are made. Therefore, one image file for output has only to be made despite plural targets for output, when the output form is the same. This eliminates preparation of wasteful image file, and makes it possible to utilize a capacity of the memory and time efficiently.

EXAMPLES

With regard to output to each outer apparatus in FIG. 1 under the structures in FIGS. 5 and 6, an occasion to output to plural printers 6, 7 and 8 will be explained concretely as Example 1, and an occasion to output to host computers such as terminal for diagnosis 3, terminal for reference 4 and image server 5 will be explained concretely as Example 2.

Example 1

Output to Printer

With respect of a unit of print output queue, when images are required to be outputted in the order in which the images were received, plural printers are not divided into each printer (output channel) but are collected to be one queue.

When outputting image 1), image 2) and image 3) in FIG. 1 respectively to printers 6 and 7, printers 6 and 8, and printers 6 and 7, the following orders are used for outputting. (For example, "1) 6" means that image 1) is outputted to printer 6.)

(1) First output queue order: 1)6, 1)7, 2)6, 2)8, 3)6, 3)7
(2) Outputting 1)6→Output queue order: 1)7, 2)6, 2)8, 3)6, 3)7
(3) Outputting 1)7→Output queue order: 2)6, 2)8, 3)6, 3)7
(4) Outputting 2)6→Output queue order: 2)8, 3)6, 3)7
(5) . . .

When an error is caused on a printer of an outer apparatus, a selection is to be made from the following two options through an error code.
(1) Retry is continued without changing the order of a queue.
(2) To move to the last of the queue.

For example, when an error is caused on printer 6 and the order of the queue is not changed in the same example as the foregoing, output is made in the following way.
(1) First output queue order: 1)6, 1)7, 2)6, 2)8, 3)6, 3)7
(2) Outputting 1)7→Output queue order: 1)6, 2)6, 2)8, 3)6, 3)7
(3) Outputting 2)8→Output queue order: 1)6, 2)6, 3)6, 3)7
(4) Returning of printer 6 from an error
(5) Outputting 1)6→Output queue order: 2)6, 3)6, 3)7
(6) Outputting 2)6→Output queue order: 3)6, 3)7
(7) . . .

When a multi-image format image is made by an automatic multi-image format in FIG. 5, each image file is outputted on a pseudo basis to multi-image format queue administrating section 53, and this multi-image format queue administrating section 53 is provided in each output channel. Therefore, administration of an input channel is necessary. This input channel is capable of being turned on and turned off.

For example, when image A is outputted to printers 6 and 7 in FIG. 1, image B is outputted to printers 6 and 8, image C is outputted to printers 6 and 7, and image D is outputted to printers 6 and 8, while, images A and C are received from the same input channel R1 (for example, image generating apparatus 1 in FIG. 1), images B and D are received from the same input channel R2 (for example, image generating apparatus 1*a* in FIG. 1), and when images A and C are outputted to printer 6 with multi-image format and images B and D are outputted to printer 6 with multi-image format, output is made in the following order. (For example, "A6" means that image A is outputted to printer 6.) Incidentally, printer 6 makes multi-image format queue of input channel R1 to be printer 6 multi-image format queue R1, and printer 6 makes multi-image format queue of input channel R2 to be printer 6 multi-image format queue R2.
(1) Output queue order: A6, A7, B6, B8, C6, C7, D6, D7
(2) Registering A6 on printer 6 multi-image format queue R1
  Output queue order: A7, B6, B8, C6, C7, D6, D7
  Printer 6 multi-image format queue R1: A6
  Printer 6 multi-image format queue R2: None
(3) Outputting A7
  Output queue order: B6, B8, C6, C7, D6, D7
  Printer 6 multi-image format queue R1: A6
  Printer 6 multi-image format queue R2: None
(4) Registering B6 on printer 6 multi-image format queue R2
  Output queue order: B8, C6, C7, D6, D7
  Printer 6 multi-image format queue R1: A6
  Printer 6 multi-image format queue R2: B6
(5) Outputting B8
  Output queue order: C6, C7, D6, D7
  Printer 6 multi-image format queue R1: A6
  Printer 6 multi-image format queue R2: B6
(6) Registering C6 on printer 6 multi-image format queue R1
  Output queue order: C7, D6, D7
  Printer 6 multi-image format queue R1: A6, C6
  Printer 6 multi-image format queue R2: B6

(7) Outputting A6 and C6 to printer 6 with multi-image format
   Output queue order: C7, D6, D7
   Printer 6 multi-image format queue R1: None
   Printer 6 multi-image format queue R2: B6
(8) Outputting C7
   Output queue order: D6, D7
   Printer 6 multi-image format queue R1: None
   Printer 6 multi-image format queue R2: B6
(9) Registering D6 on a multi-image format queue
   Output queue order: D7
   Printer 6 multi-image format queue R1: None
   Printer 6 multi-image format queue R2: B6, D6
(10) Outputting B6 and D6 to printer 6 with multi-image format
   Output queue order: D7
   Printer 6 multi-image format queue R1: None
   Printer 6 multi-image format queue R2: None When the output of image A and image C to printer 6 and the output of image B and image D to printer 6 are of the multi-image format as stated above, the output to printer 6 is not conducted even when images A and B come to the forefront on the ordinary output queue, and each multi-image format image of images A and C and images B and D is prepared with a multi-image format of a type of 1×2 (2 images in lateral 1 row and longitudinal 2 line) or of 2×1 (2 images in lateral 2 lines and longitudinal 1 line) on output image forming section 43 shown in FIG. 5 and is outputted to printer 6, after the output order of images A and B is outputted temporarily to a multi-image format queue for each of input channels R1 and R2 and is registered therein, and after each of the succeeding images C and D is outputted to its own multi-image format queue.

Incidentally, in the case of a manual multi-image format, a multi-image format image is made at the point of time when a user presses an output button, and it is handled as an image thereafter. Whether this outputted image is preserved or not can be selected by a user.

Further, in the case of a separate inspection, an end of the system and a compulsory output button which is turned on, an image file is forced to be outputted to an outer apparatus. In the case of the separate inspection, however, it is preferable that ON/OFF of the compulsory output is made to be possible. Incidentally, the compulsory output means that outputting is conducted before all images for multi-image format become complete.

Further, as explained in FIG. 6, when the same image 1) is outputted continuously to a plurality of outer apparatuses (printers 6 and 7), output formats are checked whether they are the same or not by formatting queue control section 62, and if they are the same, they are outputted without being subjected to image processing again at the output image forming apparatus 43.

Example 2

Outputting to Host Computer

A unit of an output queue of the host computer collects terminal for diagnosis 3, terminal for reference 4 and image server 5 which are shown in FIG. 1 and represent a plurality of host computer and administrates them with one queue without dividing them into each output channel as in plural host computers. A range up to preparation of output files to be outputted to the host computers is made to be under queue administration, and an upper limit is stipulated for each of the total capacity of output files and the capacity of each output channel. Further, the output files are eliminated after completion of outputting to all output channels.

When outputting image A, image B and image C respectively to host computer H1 (terminal for diagnosis 3) and host computer H2 (terminal for reference 4), host computer H1 (terminal for diagnosis 3) and host computer H3 (image server 4), and to host computer H1 (terminal for diagnosis 3) and host computer H2 (terminal for reference 4), outputting is conducted in the following sequence. (For example, "AH1" means output of image A to host computer H1 (terminal for diagnosis 3), hereafter.) BH1 and BH3 are the same in terms of format.
(1) Output queue order: AH1, AH2, BH1, BH3, CH1, CH2
(2) AH1 image file preparation→Output queue order: AH2, BH1, BH3, CH1, CH2
   Image file for output: AH1
(3) AH2 image file preparation→Output queue order: BH1, BH3, CH1, CH2
   Image file for output: AH1, AH2
(4) BH3 image file preparation→Output queue order: CH1, CH2
   Image file for output: AH1, AH2, BH3
(5) Outputting AH1→Output queue order: CH1, CH2
   Image file for output: AH2, BH3
(6) Outputting BH1→Output queue order: CH1, CH2
   Image file for output: AH2, BH3
(7) Outputting BH3→Output queue order: CH1, CH2
   Image file for output: AH2

In the aforesaid way, image files for output are prepared in output image forming section 43 in the order of output queue in FIGS. 5 and 6, and are outputted to each host computer.

Further, when output formats in plural host computers are the same format, when preparing image files for output in the order at formatting queue 61 in the way shown in FIG. 6, a format of each image is compared by formatting queue control section 62 for images to be outputted to plural output channels, and when the formats are the same as a result of the comparison, a flag to the effect of outputting to plural channels (separate tables, file names) is appended and only one image file for output is prepared. In the example stated above, an image file for output is prepared concerning image BH3, but it does not need to be prepared concerning image BH1.

When an error is caused on each host computer, image files for output are prepared up to the upper limit of the storage capacity of preserving section 41 of each output channel, independently of whether an error is caused or not. Then, at the point of the upper limit of the storage capacity of the preserving section 41, an image file for output for exclusive use of the channel is not prepared. In the case of plural channels outputting, image files are prepared for other channels, and are eliminated at the point of completion of output to other channels.

For example, when an error is caused on host computer H1 that is the same as the foregoing (BH1 and BH3 are of the same format), if the limit of capacity of the storage section of host computer H1 is exceeded after the image file for output for AH1 is prepared, each image file is outputted in the following manner.
(1) Output queue order: AH1, AH2, BH1, BH3, CH1, CH2
(2) AH1 image file preparation→Output queue order: AH2, BH1, BH3, CH1, CH2
   Image file for output: AH1
(3) AH2 image file preparation→Output queue order: BH1, BH3, CH1, CH2

Image file for output: AH1, AH2
(4) BH3 image file preparation→Output queue order: BH1, CH1, CH2
Image file for output: AH1, AH2, BH3
(5) CH2 image file preparation→Output queue order: BH1, CH1
Image file for output: AH1, AH2, BH3, CH2
(6) Outputting AH2→Output queue order: BH1, CH1
Image file for output: AH1, BH3, CH2
(7) Return of host computer H1 from errors
(8) Outputting AH1, BH1 image file preparation→Output queue order: CH1
Image file for output: BH3, CH2, BH1
(9) Outputting BH3, CH1 image file preparation→Output queue: None
Image file for output: CH2, BH1, CH1

Though the targets for output are divided into a printer and a host computer respectively in Example 1 and Example 2 in the explanation above, it is also possible to structure so that image processing apparatus 2 in FIG. 3 may be capable of outputting in parallel for a printer and a host computer in each Example. In this case, when the output format in plural host computers and/or plural printers is the same, a format of each image is compared by formatting queue control section 62 concerning images to be outputted to plural channels as shown in FIG. 6, and as a result of the comparison, the format is judged to be the same, and the comparison is checked for each printer and host computer in this case. Incidentally, an input channel is an inlet for communication, and an output channel is an outlet for communication, and each of apparatuses such as an image generating apparatus, an image processing apparatus, a host computer and a printer is allotted to each channel.

The invention has been explained as stated above, referring to the embodiments and examples to which, however, the invention is not limited and can be varied in many ways within a range of technical conception. For example, in addition to CR, medical image generating apparatuses such as CT (computed tomography) for obtaining image information by computer tomography, a radiographing apparatus employing an X-ray flat panel detector, MRI (magnetic resonance imaging: nuclear magnetic resonance apparatus), DR (digital radiography), and US (ultrasound: ultrasound diagnostic apparatus), can naturally be used as a medical image generating apparatus.

Further, in the medical network system in the invention, a plurality of medical image processing apparatuses may be included, and as a host computer, other terminal apparatuses may further be included in addition to terminal for diagnosis 3, terminal for reference 4 and image server 5 shown in FIG. 1, and plural terminals for diagnosis 3, plural terminals for reference 4 and plural image servers 5 may naturally be included.

In the medical image processing apparatus and the medical network system of the invention, a consumed storage capacity of a storage means is not increased when outputting multi-image format images, and changes of original images are reflected on multi-image format images until the moment immediately before outputting, thus, ease of operation is achieved when multi-image format images are designated. In addition, when outputting one image to plural input apparatuses, it is possible to utilize efficiently storage capacity of the storage means and time without making wasteful image files.

What is claimed is:

1. A medical image processing apparatus for receiving an image file including medical image data corresponding to a medical image and for outputting the image file with an output format, said medical image processing apparatus comprising:
   a storing section for storing a plurality of image files, including a set of plural multi-image format files designated to be formed on a single image plane in a multi-image format in which the plural multi-image format files are arranged such that each of the multi-image format files is positioned vertically or horizontally adjacent to another one of the multi-image format files in the plane of the single image plane, wherein the plural multi-image format files of the set are randomly and respectively sent to the storing section and stored among the plurality of image files;
   an output queue controlling section for controlling an output queue of the plurality of image files and for controlling the storing section to output an image file in accordance with an output queue order of the image file;
   an image processing section for receiving an image file from the storing section and for formatting the medical image data of the image file in an output format; and
   a multi-image format queue controlling section for registering a file name of a multi-image format file to be formatted in the multi-image format on the single image plane;
   wherein when a multi-image format file of the set of plural multi-image format files comes to a forefront of the output queue, the output queue controlling section outputs a file name of the multi-image format file to the multi-image format queue controlling section without outputting from the storing section the medical image data of the multi-image format file, and the multi-image format queue controlling section registers the file name of the multi-image format file;
   wherein when all file names of the set of multi-image format files are registered in the multi-image format queue controlling section, the multi-image format queue controlling section controls the storing section to output to the image processing section the medical image data of the set of plural multi-image format files; and
   wherein the image processing section formats the received medical image data of the set of plural multi-image format files such that the set of medical images of the received medical image data are displayed in the multi-image format on the single image plane.

2. The medical image processing apparatus of claim 1, further comprising:
   a format queue controlling section for controlling the image processing section in accordance with an output format for each of a plurality of output devices;
   wherein when an image file is to be outputted to at least two output devices of the plurality of output devices having a same output format, the format queue controlling section controls the image processing section to format the image file in the output format of the at least two output devices and outputs the image file in the output format to the at least two output devices.

3. The medical image processing apparatus of claim 2, wherein the format queue controlling section controls the image processing section not to delete the image file in the output format until the format queue controlling section judges that the image file in the output format has been outputted to all the at least two output devices.

4. The medical image processing apparatus of claim 2, wherein the image processing section comprises a memory to store image files to be outputted to the plurality of output devices, and wherein when an available memory capacity of the memory is less than a predetermined available memory capacity, the image processing section does not format any image files for output to the plurality of output devices.

5. The medical image processing apparatus of claim 2, wherein when the multi-image format file is to be outputted to at least one of the plurality of output devices, the format queue controlling section controls the image processing section in accordance with an output format of the at least one of the plurality of output devices.

6. A medical image processing system which is operable via a network, said medical image processing system comprising:

a storing section for storing a plurality of image files, including a set of plural multi-image format files designated to be formed on a single image plane in a multi-image format in which the plural multi-image format files are arranged such that each of the multi-image format files is positioned vertically or horizontally adjacent to another one of the multi-image format files in the plane of the single image plane, wherein the plural multi-image format files of the set are randomly and respectively sent to the storing section and stored among the plurality of image files;

an output queue controlling section for controlling an output queue of the plurality of image files and for controlling the storing section to output an image file in accordance with an output queue order of the image file;

an image processing section for receiving an image file from the storing section and for formatting the medical image data of the image file in an output format;

a multi-image format queue controlling section for registering a file name of a multi-image format file to be formatted in the multi-image format on the single image plane; and at least one output device to output an image corresponding to the image file;

wherein when a multi-image format file of the set of plural multi-image format files comes to a forefront of the output queue, the output queue controlling section outputs a file name of the multi-image format file to the multi-image format queue controlling section without outputting from the storing section the medical image data of the multi-image format file, and the multi-image format queue controlling section registers the file name of the multi-image format file;

wherein when all file names of the set of multi-image format files are registered in the multi-image format queue controlling section, the multi-image format queue controlling section controls the storing section to output to the image processing section the medical image data of the set of plural multi-image format files; and wherein the image processing section formats the received medical image data of the set of multi-image format files such that the set of medical images of the received medical image data are displayed in the multi-image format on the single image plane, and outputs the formatted medical image data of the set of multi-image format files to the at least one output device.

7. The medical image processing system of claim 6, wherein the at least one output device comprises a plurality of output devices, and the medical image processing system further comprising:

a format queue controlling section for controlling the image processing section in accordance with an output format for each of the plurality of output devices;

wherein when an image file is to be outputted to at least two output devices of the plurality of output devices having a same output format, the format queue controlling section controls the image processing section to format the image file in the output format of the at least two output devices and outputs the image file in the output format to the at least two output devices.

* * * * *